(12) United States Patent
Nowak et al.

(10) Patent No.: US 7,172,878 B1
(45) Date of Patent: Feb. 6, 2007

(54) METHOD FOR DETERMINING THE CONCENTRATION OF THROMBIN INHIBITORS AND KITS THEREFOR

(75) Inventors: Gotz Nowak, Jena (DE); Elke Bucha, Erfurt (DE)

(73) Assignee: Haemosys GmbH, Jena (DE)

( * ) Notice: Subject to any disclaimer, the term of this patent is extended or adjusted under 35 U.S.C. 154(b) by 0 days.

(21) Appl. No.: 09/890,654

(22) PCT Filed: Jan. 28, 2000

(86) PCT No.: PCT/DE00/00330

§ 371 (c)(1),
(2), (4) Date: Nov. 5, 2001

(87) PCT Pub. No.: WO00/46602

PCT Pub. Date: Aug. 10, 2000

(30) Foreign Application Priority Data

Feb. 4, 1999 (DE) .................................. 199 04 674

(51) Int. Cl.
*C12Q 1/56* (2006.01)

(52) U.S. Cl. ......................................................... 435/13
(58) Field of Classification Search ................... 435/13
See application file for complete search history.

(56) References Cited

U.S. PATENT DOCUMENTS

| 5,529,905 A | 6/1996 | Lang et al. |
| 5,547,850 A | 8/1996 | Nowak et al. |
| 5,702,912 A * | 12/1997 | Hemker et al. ................ 435/13 |

FOREIGN PATENT DOCUMENTS

| DE | 2661080 C2 | 2/1990 |
| DE | 42 03 980 A1 | 8/1993 |
| DE | 199 04 674 A1 | 8/2000 |
| EP | 0 570 355 A | 11/1993 |
| EP | 0570355 A | 11/1993 |

OTHER PUBLICATIONS

Houbouyan et al., "Inhibition of thrombin generation by heparin and LMW heparins: a comparison of chromogenic and clotting methods", Blood Coagulation and Fibrinolysis 7 : 24-30 (1996).*
Han Jin-Hua et al: "Inhibition of meizothrombin and meizothrombin(desF1) by heparin cofactor II." Journal of Biological Chemistry, vol. 272, No. 45, Nov. 7 1997, pp. 28660-28665.
Doyle M.F. et al.: "Multiple active forms of Thrombin IV. Relative Activities of Meizothrombins" Journal of Biological Chemistry, vol. 265, No. 18, 1990, pp. 10693-10701.
Abstract: 87 :196026 Amidolytic assay of promthrombin activated with ecarin, a procoagulant from Exhis carinatus venom, 7-Enzymes, vol. 87, 1977; 196035.
"Role of Meizothrombin and Meizothrombin-(des F1) in the Conversion of Prothrombin to Thrombin by the *Echis carinatus* Venom Coagulant", Moo-Jhong Rhee et al., Biochemistry 1982, 21, 3437-3443.

* cited by examiner

*Primary Examiner*—Sandra Saucier
(74) *Attorney, Agent, or Firm*—Millen, White, Zelano & Branigan

(57) ABSTRACT

The invention relates to a method for determining the concentration of thrombin inhibitors in a non-turbid body liquid or a non-turbid extract from a body liquid. It comprises the following steps. The body liquid is taken from a living body, and the body liquid is subjected to a separation from the turbid matter, if necessary. To the non-turbid body liquid thus obtained are added a coagulation-inhibiting substance not interfering in the transformation prothrombin/active meizothrombin or Mtdesfgl, resp., a chromogenic or fluorogenic substrate not dissociable by active meizothrombin or Mtdesfgl, resp., and a substance dissociating prothrombin into meizothrombin or Mtdesfgl, resp., and as an optional prothrobmin. The thus obtained solution or mixture, resp., is subjected to a wavelength-selective light absorption or light emission measurement as a function of the time. From the reduction of the light absorption or light emission per time unit is determined the amount of the thrombin inhibitor included in the body liquid by comparison to previously determined standard curves.

Figure 1:
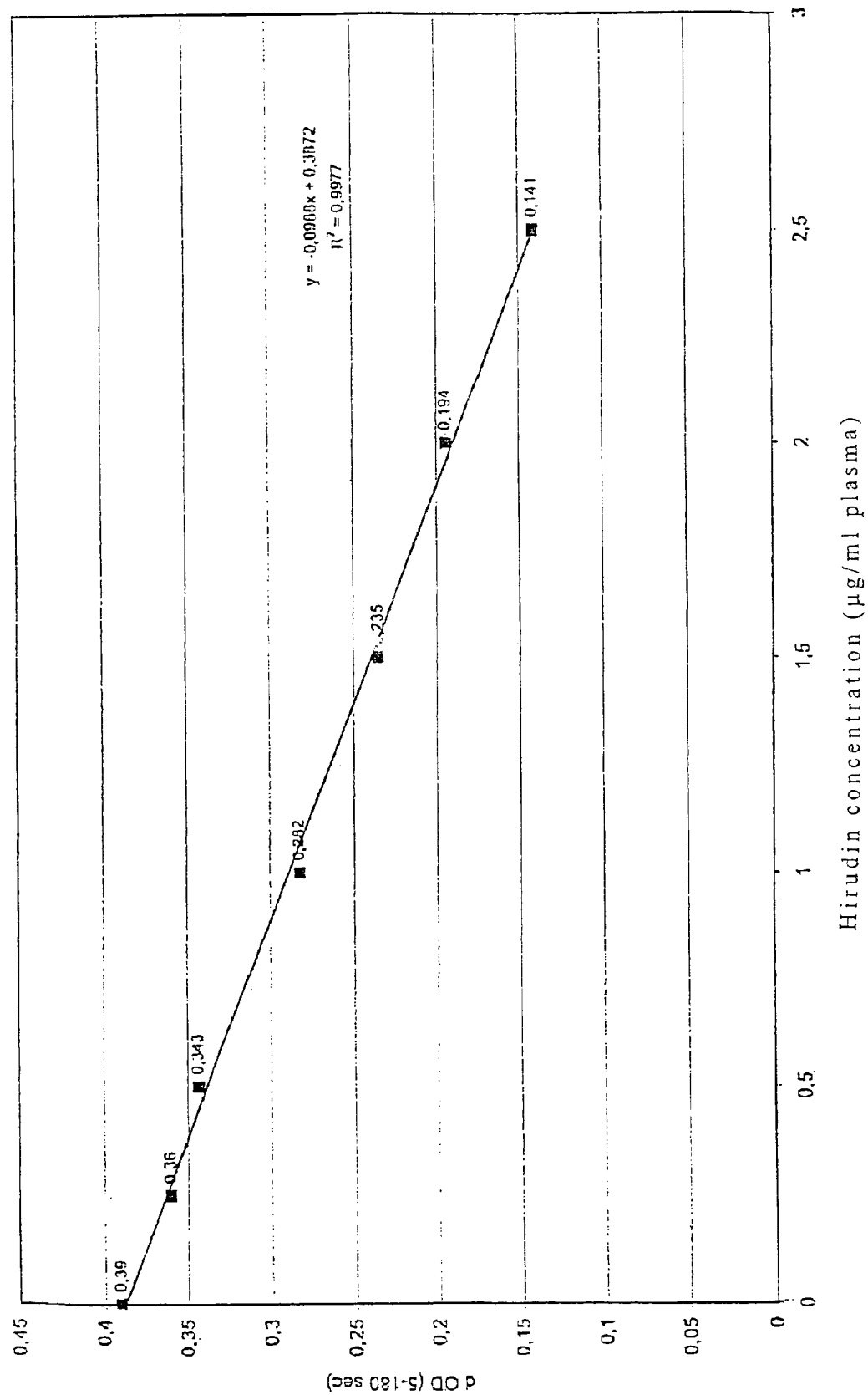

6 Claims, 1 Drawing Sheet

METHOD FOR DETERMINING THE CONCENTRATION OF THROMBIN INHIBITORS AND KITS THEREFOR

The invention relates to a method for determining the concentration of thrombin inhibitors, wherein body liquid is taken from a living body and wherein a substance separating prothrombin into meizothrombin or meizothrombin-des fragment 1 (in the following Mtdesfgl) is added to said body liquid. As thrombin inhibitors are understood all natural or synthetic substances directly inhibiting thrombin or initial thrombin products. An example for a natural thrombin inhibitor is hiruidin, extracted from the saliva of hirudo medicinalis. Hirudin is a very small protein composed of 65 amino acids and having a molecular weight of 7 kD. Examples for synthetic thrombin inhibitors are the so-called hirulogs comprising partial sequences being analogous or homologous to hiruidin, and polypeptides composed of or comprising a tripeptide Phe-Pro-Arg or derivatives of such a tripeptide, such as boric acid derivatives, chloromethylketon derivatives, benzamidine derivatives, argininals, amino acid modified derivatives and the like. The above substances have probably the same mechanism effects as hirudin. As donors of the body liquid are possible human beings and mammals, such as rodents. Examples for body liquids are in particular blood or blood plasma produced from blood. But other body liquids not containing prothrombin are also possible, for instance urine, liquor, saliva, peritoneal liquid and others. Then, according to the invention, prothrombin is added. Non-turbid means that there should be no substantial amounts of suspended particles in the body liquid to be examined. This can be achieved, if necessary, by centrifugation of the body liquid and separation of the remainder.

The theoretical background the invention is based on is the following. The transformation of prothrombin into thrombin is an essential factor for blood coagulation. Thrombin acts on the creation of fibrin monomers from fibrinogen and on the polymerization of the fibrin monomers. Prothrombin is transformed into thrombin with the contribution of activated factor X, activated factor V Ca" ions and phospholipids, such as platelet factor 3. A multi-step reaction takes place, with intermediates being formed in relatively small amounts. If however the coagulation is initiated by means of for instance ecarin or another snake venom or snake venom fraction, an "atypical" intermediate will be formed, such as meizothrombin, PIVKA meizothrombin or meizothrombin-des fragment 1 (PIVKA is the abbreviation for a protein being induced by a vitamin K antagonist). These atypical intermediates interestingly are inactivated for instance by hirudin, not however by haprin (factors IIa, IXa, XIa, XIIa inhibitor and/or antithrombin). Besides, they will also lead to thrombin formation and subsequently to coagulation. The affinity of hiruidin and other synthetic thrombin inhibitors to the atypical intermediates is very high ($k_i > 10^{-10}$ mol/l for meizothrombin), so that the free atypical intermediate is temporarily bound by the thrombin inhibitor.

The above fundamentals are used in a method of the type referred to above, described in document U.S. Pat. No. 5,547,850, wherein so to speak the consumption of the thrombin inhibitor is detected by measurement of the delay of coagulation. A large amount of thrombin inhibitor will lead to a long time before the beginning of coagulation, and vice versa. In principle, this method has proven successful in practical applications. The drawbacks however are that in cases of reduced fibrinogen level, falsifications may occur, since a (too) low fibrinogen level, same as a high thrombin inhibitors level, may lead to long coagulation times.

The invention is based on the technical object to specify a method for determining the concentration of thrombin inhibitors, said method providing precise values independently from the fibrinogen level.

For achieving this object, the invention teaches a method for determining the concentration of thrombin inhibitors in a non-turbid body liquid or a non-turbid extract from a body liquid, comprising the following steps: a) the body liquid is taken from a living body, and the body liquid is subjected to a separation from the turbid matter, if necessary, b) to the non-turbid body liquid obtained in step a) are added a coagulation-inhibiting substance not interfering in the transformation prothrombin/active meizothrombin or Mtdsfgl, resp ., a chromogenic or fluorogenic substrate not dissociable by active meizothrombin or Mtdesfgl, resp., and a substance dissociating prothrombin into meizothrombin or Mtdesfgl, resp., and as an option prothrombin, c) the solution or mixture, resp., obtained in step b) is subjected to a wavelength-selective light absorption or light emission measurement as a function of the time, d) from the reduction of the light absorption or light emission in step c) per time unit is determined the amount of the thrombin inhibitor included in the body liquid by comparison to previously determined standard curves. Alternatively to the substance dissociating prothrombin into meizothrombin or Mtdesfgl, resp., or as a complement hereto, meizothrombin or Mtdsesfgl, resp., may be added. Further, the invention teaches a method for determining the (specific) activity of thrombin inhibitors (for inhibiting generated meizothrombin or Mtdesfgl, resp.) in a non-turbid aqueous liquid, comprising the following steps: a) a body liquid is taken from a living body, and the body liquid is subjected to a separation from the turbid matter, if necessary, or a non-turbid liquid is synthetically produced, b) to the non-turbid body liquid obtained in step a) are added a given amount of thrombin inhibitor, if applicable a coagulation-inhibiting substance not interfering in the transformation prothrombin/active meizothrombin or Mtdesfgl, resp., a chromogenic or fluorogenic substrate not dissociable by active meizothrombin or Mtdesfgl, resp., and a substance dissociating prothrombin into meizothrombin or Mtdesfgl, resp., or meizothrombin or Mtdesfgl, resp., and as an option prothrombin, c) the solution or mixture, resp., obtained in step b) is subjected to a wavelength-selective light absorption or light emission measurement as a function of the time, d) from the reduction of the light absorption or light emission in step c) per time until is determined the activity of the thrombin inhibitor by comparison (of the negative slope) to previously determined standard curves. As chromogenic substrates are designated substances containing chromophoric groups and being specifically dissociated by thrombin, resulting in a coloration. Fluororgenic substances are substances that are specifically dissociated by thrombin, resulting in fluorescent substances. Prothrombin may be added, if the body liquid does not naturally contain sufficient prothrombin, for instance in the case of vitamin K deficiency, or if the amount of thrombin inhibitor to be expected or the activity of the thrombin inhibitor will recommend so, or if during an illness a prothrombin deficiency has occurred.

The invention is based on the surprising detection that chromogenic or fluorogenic substances being specifically dissociated by thrombin are equally specifically dissociable measurement as a function of the time, d) by meizothrombin or Mtdesgfl, resp. This could not be expected since intermediates are necessary pre-steps, however do not naturally develop the same effects or reactivities as the thrombin. By that the detecting reaction according to the invention exclusively takes place by monitoring the meizothrombin or Mtdesfgl inhibition, resp., by means of a color reaction, the detection is completely independent from the fibrinogen level. Rather, for body liquids, in particular blood or blood plasma, the coagulation has even to be prevented, in order to not disturb the color reaction evaluation. In addition, the determination of the concentration of the thrombin inhibitors is in all sections at least as accurate as the determination by means of the prior art method at a high fibrinogen level. Also, there is independence from any orally administered anti-coagulation possibly included in the liquid. Further advantages are: quick measurement within minutes in chromogenic channels of conventional automatic coagulation devices (these often measure a turbidity at several wavelengths for the purpose of correction and therefore usually offer the possibility of the wavelength-selective and wavelength-variable light absorption measurement); high reproducibility of the found values because of very little variation of the individual values (the confidence interval is according to a multitude of test series below 5%, usually 2.2–3.5%); the high accuracy or reproducibility is further also achieved at very high thrombin inhibitor or hirudin levels, resp.; due to above features the method according to the invention is suitable for national and international standardization.

The method according to the invention is used on one hand in science, namely in all areas of examinations where concentrations of thrombin inhibitor have to be determined, and for the (if applicable, high-capacity) screening of prospective thrombin inhibitors. In the latter case, a multitude of synthetic prospective inhibitors can be examined with a high throughput with regard to their actual effects. Activity means here the determination whether at all an inhibition takes place, and if yes, how the kinetics or the specific activity are. On the other hand, clinical application is also a issue, for instance for monitoring the thrombin inhibitor levels of patients to whom the inhibitor is administered for therapeutical reasons. Thus it can be prevented, in a simple and economical way, that an under or over-dosage of the thrombin inhibitor takes place, and that in quasi-continuous or discontinuous monitoring.

In detail, the substance not interfering in the transformation prothrombin/active meizothrombin or Mtdesfgl, resp., may be selected from the group "calcium-complex forming agents, heparin, heparinoids, anti-thrombin III, protein C, fibrin polymerization inhibiting substances and mixtures of such substances". A specific example for this is Pefabloc FG manufactured by Pentapharm A; Bale, Switzerland, this substance being a tetrapeptide (Gly-Pro-Arg-Pro) and preventing the fibrinogen polymerization with a high affinity. The substance dissociating prothrombin into meizothrombinor Mtdesfgl, resp., may be selected from the group of the snake venoms or snake venom fractions, for instance venoms of dispholidus, rhabdophis, bothrops, notechis, oxyuranus an Russel's vipers. Suitably cleaned fractions therefrom are used. Preferably, ecarin, a highly cleaned fraction of the echis-carinatus toxin, or multi-squamase the prothrombin dissociating enzyme from echis multi-squamatus, is used. Such substances as for instance ecarin are commercially available from Pentapharm AG, Switzerland, among other sources.

The chromogenic substrate dissociable by active meizothrombin or Mtdesfgl, resp., may release p-nitroaniline under dissociation, and the light absorption measurement can then be performed at 405 nm. Examples for such or even other substrates are tripeptides available under the name Chromozym TH or Pefachrom TH from the companies Chromogenix, Boehringer, Pentapharm (Pefachrome TH is H-D-ChG-Ala-Arg-pN.2AcOH). An example for fluorochromic substrates is Pefachrom TH fluorogen, being available under the name Pefa 15865 from the company Pentapharm.

In detail, it is recommended for the activities in question to perform in step c) a first absorption or emission measurement after 0–100 s, preferably 0–50, most preferably 5–15 s, and a second one after another 10–1,000 s, preferably 50–500 s, most preferably 150–300 s, measured from the addition of the substance dissociating prothrombin into meizothrombin or Mtdesfgl, resp. The method according to the invention is particularly suited for the determination of hirudin or the determination of the concentration and/or the activity of synthetic thrombin inhibitors or hirulogs.

The invention also relates to a test kit for determining the concentration of thrombin inhibitors in a non-turbid body liquid or a non-turbid extract from a body liquid, comprising the following kit components: K1) a solution of a coagulation-inhibiting substance not interfering in the transformation prothrombin/active meizothrombin or Mtdesfgl, resp., K2) a chromogenic or fluorogenic substrate dissociable by active meizothrombin or Mtdesfgl, resp., and K3) a solution of a substance dissociating prothrombin into meizothrombin or Mtdesfgl, resp., wherein components K3) may be replaced or complemented by a component K3a) of a solution with meizothrombin or Mtdesfgl, resp., and a test kit for determining the activity of thrombin inhibitors in a non-turbid body or in a non-turbid extract from a body liquid or in a non-turbid non-natural aqueous liquid, comprising the following kit components: as an option K1) a solution of a coagulation-inhibiting substance not interfering in the transformation prothrombin/active meizothrombin or Mtdesfgl, resp., K2) a chromogenic or fluorogenic substrate dissociable by active meizothrombin or Mtdesfgl, resp., and K3) a solution of a substance dissociating prothrombin into meizothrombin or Mtdesfgl, resp., wherein component K3) may be replaced or complemented by a component K3a) of a solution with meizothrombin or Mtdesfgl, resp. The kit components may be separated from each other or provided in a single test kit package. Further, as an optional additional kit component, a solution with prothrombin may be provided.

In any case it is understood that for the addition of substances dissociating thrombin, meizothrombin or Mtdesfgl, resp., and/ormeizothrombin or Mtdesfgl, resp., these are used in defined, given amounts. Corresponding considerations apply to the substrate.

Based on the method according to the invention and being particularly well suited for screening purposes, further subject matter of the invention are thereby formed or characterized new thrombin inhibitors, which are namely available by the following steps: A) elements of a group of prospective thrombin inhibitors are submitted subsequently or separately and simultaneously in a given and preferably identical concentration to the method, B) the reduction of the light absorption or light emission per time unit is determined for each prospective thrombin inhibitor and compared to the light absorption or light emission per time unit of a given, preferably identical concentration or hirudin determined under identical conditions, C) those prospective thrombin inhibitors are selected the reduction of the light absorption or light emission of which per time unit corresponds to at least 10% of the corresponding reduction when hirudin is used.

For the test kit according to the invention and the thrombin inhibitors found according to the invention apply the detailed explanations as given above for the method according to the invention.

As far as meizothrombin or Mtdesfgl, resp., is used, this can commercially be bought, for instance from Pentapharm AG, Switzerland, can however also be provided at immobilized ecarin according to the statement in document U.S. Pat. No. 5,547,850.

The devices to be used for the invention as for instance semi or fully automatic coagulation devices being present anyway. These may for instance be automatic coagulation analyzers of the type Sysmex CA-500 or S2000 of the company Dade-Beharing or of the type Electra 2000. In the CA-500, the light emitted by a LED is sent through a filter (405 nm) and then through the sample. The CA-500 determines in the chromogenic channel the variations or reduction of the light absorption of dyes, as for instance pNA (p-nitroaniline). If there is for instance hirudin in a sample, the generated or added meizothrombin or Mtdesfgl, resp., is inactivated, with the consequence of a thereby inhibited pNA release. The as such differently behaving (changing) optical density of the sample is recorded by a photodiode, and is evaluated. The monitored change in the light absorption is inversely proportional to the hirudin activity.

In the following, the invention will be explained in more detail, based on experiments representing examples of execution only.

For the determination of a standard curve, pooled human citrate plasma was treated with given amounts of hirudin solution. The thus obtained standard solutions were measured in a CA-500.

As reagents were filled in:
Reagent 1 [inhib] (room temperature): 400 µl Pefabloc FG (20 mM; dissolved in 0.9% NaCl)+2,100 µl Tris buffer;
Reagent 2 [chromo] (room temperature): Pefachrome TH (10 µmol/vial), diluted for 3 µmol/ aq. dest,
Reagent 3 [ecarin] (150° C.): ecarin (50 EU/vial), diluted to 0.3 EU/ml (the contents of the ecarin bottle are dissolved in 5 ml of 0.9% NaCl solution and shortly prior to application set to the final concentration with a 1:2 mixture of 0.9% NaCl, containing 1% Prionex (Merck) and 0.1 M CaCl$_2$ solution.

The test records are shown below. As dil. buffer was used a mixture of 16.6 µl prothrombin (cleaned; protein content 2.22 mg/ml) and 984 µl of a mixture of 900 µl Tris buffer (0.05 M, pH 8, 37° C., +0.1 M NaCl) and 100 µl Prionex (Merck).

| Test records | Name | Ecch | |
|---|---|---|---|
| Detector | | | Chrome |
| Start Point | | | 5 sec |
| End Point | | | 180 sec |
| Sensitivity | | | Low Gain |
| 1 Sample Vol. | | Citrate plasma | 5 µl |
| Dil. Vol. | | Buffer | 70 µl |
| 2 Sample Vol. | | | 0 µl |
| ***** | | | 0 µl |

-continued

| Test records | Name | Ecch | |
|---|---|---|---|
| Reagent 1 | | Inhib | 30 sec |
| Reag. Vol. | | | 125 µl |
| Rinse | | | 125 µl |
| Reagent 2 | | Chromo | 120 sec |
| Chromo | | | 20 µl |
| Rinse | | | 100 µl |
| Reagent 3 | | Ecarin | 210 sec |
| Reag. Vol. | | | 20 µl |
| Rinse | | | 50 µl |

(Rinse: 1% sodium hypochlorite solution)

FIG. 1 shows the obtained standard curve. The extremely good correlation coefficient of 0.9977 is conspicuous. In the experiment, just replace the standard sample by the sample to be determined, and read the unknown hirudin concentration in FIG. 1 from the measured reduction of the optical density.

The invention claimed is:

1. A single test kit package for determining the concentration of thrombin inhibitors in a non-turbid body liquid or a non-turbid extract from a body liquid, comprising the following components: K1) a solution of a coagulation-inhibiting substance not interfering in the transformants of prothrombin into active meizothrombin or meizothrombin-des fragment 1, wherein said coagulation-inhibiting substance is a fibrin polymerization inhibiting substance: K2) a chromogenic or fluorogenic substrate dissociable by active meizothrombin or meizothrombin-des fragment 1; and K3) a solution of a substance dissociating prothrombin into meizothrombin or meizothrombin-des fragment 1.

2. A single test kit package for determining the activity of thrombin inhibitors in a non-turbid body or in a non-turbid extract from a body liquid or in a non-turbid non-natural aqueous liquid, comprising the following kit components: K1) a chromogenic or fluorogenic substrate dissociable by active meizothrombin or meizothrombin-des fragment 1; K2) meizothrombin or meizothrombin-des fragment 1; and K3) a solution of a coagulation-inhibiting substance not interfering in the transformation of prothrombin into active meizothrombin or meizothrombin-des fragment 1, wherein said coagulation-inhibiting substance is a fibrin polymerization inhibiting substance.

3. A test kit according to claim 1, further comprising providing a solution of prothrombin.

4. A kit package of claim 1, further comprising meizothrombin or meizothrombin-des fragment 1.

5. A single test kit package of claim 1, wherein the fibrin polymerization inhibiting substance is a Gly-Pro-Arg-Pro tetrapeptide.

6. A single test kit package of claim 2, wherein the fibrin polymerization inhibiting substance is a Gly-Pro-Arg-Pro tetrapeptide.

* * * * *